(12) United States Patent
Klare et al.

(10) Patent No.: US 7,514,477 B2
(45) Date of Patent: Apr. 7, 2009

(54) LOW-VISCOSITY RADIATION-CURABLE COMPOSITION FOR MAKING AN EARPIECE

(75) Inventors: Martin Klare, Dortmund (DE); Reiner Altmann, Castrop-Rauxel (DE); Michael Kutschinski, Castrop-Rauxel (DE); Thomas Veit, Munster (DE)

(73) Assignee: Derve-Otoplastik GmbH, Unna (DE)

( * ) Notice: Subject to any disclaimer, the term of this patent is extended or adjusted under 35 U.S.C. 154(b) by 254 days.

(21) Appl. No.: 11/546,943

(22) Filed: Oct. 12, 2006

(65) Prior Publication Data
US 2007/0100090 A1    May 3, 2007

(30) Foreign Application Priority Data
Oct. 18, 2005    (DE) ................. 10 2005 050 186

(51) Int. Cl.
| | |
|---|---|
| G03C 5/00 | (2006.01) |
| G03F 7/00 | (2006.01) |
| C08K 3/28 | (2006.01) |
| C08L 33/10 | (2006.01) |
| B29C 35/08 | (2006.01) |

(52) U.S. Cl. ................. 522/81; 522/83; 522/96; 522/64; 430/269; 264/401

(58) Field of Classification Search ............... 430/269; 264/401; 522/81, 83, 96
See application file for complete search history.

(56) References Cited

U.S. PATENT DOCUMENTS

| | | | |
|---|---|---|---|
| 5,763,503 A * | 6/1998 | Cowperthwaite et al. ...... 522/44 |
| 6,475,631 B1 * | 11/2002 | Yamamoto et al. ........... 428/480 |
| 6,579,533 B1 * | 6/2003 | Tormala et al. .............. 424/426 |
| 6,829,362 B1 * | 12/2004 | Kadziela et al. .............. 381/312 |
| 7,098,256 B2 * | 8/2006 | Ong et al. ...................... 522/97 |
| 7,232,646 B2 * | 6/2007 | Klare et al. ............... 430/285.1 |
| 2007/0122356 A1 * | 5/2007 | Kessler et al. ................. 424/49 |

FOREIGN PATENT DOCUMENTS

WO  WO 2005/001570  * 1/2005

* cited by examiner

*Primary Examiner*—Susan W Berman
(74) *Attorney, Agent, or Firm*—Andrew Wilford

(57) ABSTRACT

A biocompatible, low-viscosity, radiation-curable composition for producing antimicrobial earpieces contains:

a) 20-75 wt. % of one or a plurality of monomeric/oligomeric urethane(meth)acrylates having an acrylate functionality of <4, viscosity <30 Pa s, and molecular weight <3500;

b) 5-45 weight % of a monomeric or oligomeric dimethacrylate of bisphenol A or bisphenol F and or of a monomeric aliphatic or cycloaliphatic di(meth)acrylate having a viscosity <6 Pa s;

c) 2.5-25 weight % of a cross-linking monomeric or oligomeric component containing 4 methacrylate and/or acrylate functionalities;

d) 0-15 wt. % of one or a plurality of monofunctional (meth)acrylates;

e) 0.01-5 wt. % of one or a combination of antimicrobially active glass fillers and silver particles; and f) 0.5-6 wt. % of one or a plurality of photoinitiators whose absorption is in the wavelength range of an ND:YVO$_4$ laser beam used or of an actinic radiation source used to promote free radical formation.

3 Claims, No Drawings

LOW-VISCOSITY RADIATION-CURABLE COMPOSITION FOR MAKING AN EARPIECE

The present invention relates to low-viscosity, radiation-curable compositions for producing technical medical products having antimicrobial properties, in particular for producing earpieces that are produced by means of the PNP method (U. Voogdt, "Otoplastik," 2nd edition, volume 2, Median Verlag, Killisch-Horn GmbH, p. 22ff (1998) or a regenerative method such as for instance stereolithography, based on at least two compounds that have radically polymerizable (meth)acrylate functions, and at least one photoinitiator that is suitable for the polymerization of the suitable compounds, and at least one inhibitor intended for stabilizing the compositions, and at least one or a combination of antimicrobially or bacteriostatically acting components that are characterized in that it is a bioactive glass filler, silver ion-releasing, nano-scale silver powder, or a polymerizable compound having antimicrobial properties.

In such PNP (positive-negative-positive) methods, in a first step the professional in the hearing field takes an ear impression (positive) for producing an otoplastic (for devices worn behind the ear) or a shell (for devices worn in the ear). In a second step, casting creates a negative mold (N) in which the radiation-curable low-viscosity composition is subsequently cast and then irradiated. The earpiece (positive) produced in this manner must be fitted to the auditory canal as well as possible. Otherwise, poorly fitting molds would cause problems (for instance pressure points) and have a negative impact on hearing aids (e.g. feedback). Consequently, it is important that the composition have the lowest possible viscosity, that is, "that it flows well," so that the material can fill in undercuts and very fine surface textures and thus be cast in the final product.

It is known from U.S. Pat. No. 4,575,330 that low-viscosity, radiation-curable resins or resin mixtures can be used for producing three-dimensional objects by means of stereolithography. Moreover, it is known from U.S. Pat. No. 5,487,012 and WO 2001/087001 that stereolithography can be used advantageously for producing earpieces. In the stereolithographic method, three-dimensional objects are created from a low-viscosity, radiation-curable composition in that each thin layer (approx. 0.0025-0.1 mm) of the composition is precured by means of actinic radiation in a defined manner such that the created layer has the desired sectional shape of the object at this location. At the same time, the layer generated is polymerized on the layer cured in the preceding step. Thus the entire item can be produced using a computer-controlled laser system such as for instance an Nd:YVO$_4$ solid-state laser (Viper si$^2$ system, 3D Systems Corporation, US). The generated shaped body is likewise post-cured for instance by irradiation.

Special requirements are imposed on the resin compositions that can be used in the stereolithographic process. In particular, these include the radiation sensitivity and viscosity of the resin compositions, as well as the strength of the shaped body precured by means of laser curing. In stereolithography this shaped body that is not completely cured is called a green compact, and the strength of this green compact, characterized by E-module and flexural strength, is called green strength. Green strength represents an important parameter in stereolithography because shaped bodies with low green strength deform under their own weight during the stereolithography process or can slump or sag during subsequent curing for instance with a xenon arc lamp or halogen lamp. It is therefore understandable that in taking the above-described considerations into account compositions are used that are complicated to match and compositionte.

For instance, in Rev. Sci. Instrum. 52 (11), 1170-1173 (1981), H. Kodama discloses a low-viscosity, radiation-curable resin composition that comprises an unsaturated polyester, an acrylic acid ester, styrene, and a polymerization initiator. With respect to use in stereolithography, however, this resin composition has low green strength and unsatisfactory photosensitivity. The resin compositions disclosed in U.S. Pat. No. 4,100,141 also have unsatisfactory photosensitivity in terms of production engineering. Low photosensitivity means that long periods are required for producing the shaped bodies. Consequently, the photosensitivity of the stereolithography resin compositions must be adjusted such that, from the ratio of the achieved laser beam penetration depth into the low-viscosity radiation-curable resin composition and the radiation energy applied, using low radiation energy, the greatest possible curing depth is attained while at the same time a high degree of polymerization, good green strength, and adequate stability of the resin composition against autopolymerization are realized. U.S. Pat. No. 5,476,748 and WO 99/50711, for instance, describe liquid radiation-curable compositions that partially satisfy the above-described requirements. However, these compositions, called "hybrid systems," contain a combination of radically and cationically polymerizable components. They comprise first a liquid, di- or polyfunctional epoxy compound or a mixture comprising difunctional or higher-functional epoxy compounds; second a cationic photoinitiator or a mixture of cationic photoinitiators; third a photoinitiator or a mixture of photoinitiators for free radical polymerization and at least one low-viscosity poly(meth)acrylate having a (meth)acrylate functionality of n>2, at least one diacrylate and one polyol component from the group of hydroxyl-terminated polyether, polyester, and polyurethanes. One skilled in the art is familiar with the fact that in terms of toxicological aspects such compositions must be evaluated critically and consequently cannot be used, or can only be used in a limited capacity, for producing medical products. This is also true of compounds with epoxide functions that are used in such compositions. One skilled in the art is furthermore familiar with the fact that many acrylate compounds—in particular short-chain acrylate compounds—likewise possess an elevated allergy potential and thus resin compositions such as are described e.g. in EP 0425441, EP 0914242, and EP 0579503 cannot be used for producing e.g. earpieces due to biocompatibility issues. Monomeric or oligomeric dimethacrylates based on bisphenol A or bisphenol F and urethane methacrylates having an acrylic functionality of n is greater than or equal to 2 have proved themselves for use in medical technology. However, compared to the group of acrylate compounds, the group of methacrylate compounds have lower reactivity for stereolithography. This results in the disadvantages, cited in the foregoing, in terms of laser beam penetration depth and green strength of the precured articles. Moreover, due to the reduced reactivity of this class of compounds, higher concentrations of one or a plurality of photoinitiators must be used for the free radical polymerization. This results in reduced stability against autopolymerization of the resin composition. Moreover, one skilled in the art is familiar with the fact that there is increased mechanical and thermal loading of the stereolithographic resin composition when producing a large number of small articles of low mass, and this can lead to autopolymerization of the stereolithographic resin or to changing properties in the resin composition and the shaped body generated therefrom. For one thing, this is the result of the fact that when resin consumption is low the precured shaped bodies fixed on a platform have to be removed from the construction area of the stereolithograpy system relatively frequently. This results in temperature fluctuations in the stereolithography resin in the construction area. In addition, during production of earpieces there is a relatively large surface-area/volume ratio for the shaped bodies generated. One skilled in the art will be aware of the fact that in free radical polymerization an inhibition layer remains on the surface of the shaped bodies due to oxygen access. Thus, the resin, which is not completely polymerized, can dissolve from the surface of the specimen body into the stereolithography resin during the construction process. Another important point regarding such a composition is the flexibility of the shaped bodies obtained. One skilled in the art is familiar with the fact that commercially obtainable compositions that are sufficiently biocompatible for the above-described applications are brittle. The mean elongation values for cured articles are between 4-8% (DIN EN ISO 178). Given elevated mechanical stress, the generated earpieces can fracture, which can lead to fragments with sharp edges. This is undesirable in terms of an elevated risk of injury. Various strategies have been pursued to solve these problems, such as the use of monofunctional diluter monomers (JP 97-431498) or the use of monomeric or oligomeric low-viscosity urethane acrylates (DE 4,138,309). Substances with increased flexibility can be obtained by using the above-described components. However, the compositions cited in the foregoing result in disadvantages such as increased shrinkage and increased water absorption, and low-viscosity urethane acrylates result in an elevated allergizing potential. Moreover, the use of polyether polyols (WO 1997/038354) for reducing the cross-linking density of the 3-dimensional polymer network is described for reducing the brittleness of shaped bodies. Among the disadvantages of this method, however, are a loss of strength and a significant reduction in the water and moisture stability of the generated shaped bodies. It can be seen from this that minimizing the viscosity of the radiation-curable resin composition while retaining biocompatibility and acceptable chemic-physical and mechanical properties of the generated shaped bodies is a significant parameter in the production of earpieces by means of the P.P. method and stereolithographic technology. From stereolithography production engineering considerations it is moreover desirable that both the laser beam penetration depth and the critical energy of the stereolithography resin composition of the application can also be adjusted. Today, in many cases earpieces produced in this manner are coated both for aesthetic reasons and for reasons of cleaning and wearer comfort. Largely coatings based on methyl methacrylate, gilt, or systems produced by means of sol gel technology, as described in DE 10219679, are used for this. The latter are sold commercially e.g. by the Audio Service Company. The generated earpieces are in immediate contact with the skin of the ear, the moist and warm "climate" in the auditory canal offering nearly ideal conditions for the growth of bacteria and fungi. Inflammations can result if there are pressure points due to the earpiece or to friction between it and the skin due to for instance chewing. It is therefore desirable for the coatings to be antibacterial. The Audioservice Company offers one commercial solution, called ComforMed, that is based on the bactericidal and fungicidal effects of silver. However, the coating process is quite complex in terms of manual labor and equipment and is thus expensive. Moreover, applying a coating—the thickness of the layers is approx. 20 to 60 μm—permanently alters the shape of the generated earpiece. Consequently the layer thickness of the coating must be accounted for using a virtual offset, even when the earpiece is being produced. For avoiding these complex production steps it is therefore desirable to provide a material for manufacturing earpieces that is antimicrobial and consequently does not require any coating, and on the other hand leads to the most homogenous and smooth surfaces possible in the P.P. method and in particular in the above-described generative production methods.

The object of the present invention is to make available a resin composition for the production of medical products, in particular earpieces, by means of conventional PNP technology and by means of generative production methods such as stereolithography (SLA) and Direct Light Processing (DLP) that, first, is antimicrobially effective and that also satisfies the mechanical requirements imposed on the above-described method. These include antimicrobial activity, the mechanical requirement, particularly an elongation of ≧10%, and the requirements placed on the process named above.

Surprisingly, it was found that a low-viscosity resin mixture that comprises a urethane(meth)acrylate with a functionality n<4 and viscosity >7 and <20 Pa s, which also has one or a plurality of monomeric or oligomeric di(meth)acrylates based on bisphenol A or bisphenol F, and furthermore contains one or a combination of antimicrobially or bacteriostatically acting components can be used for the PNP method or stereolithography or DLP and that curing by means of laser results in shaped bodies that are characterized by high green strength.

In particular by adding glass filler that is antimicrobially active in the presence of moisture and that ranges in concentration from 0.5 to <5 wt. %, low-viscosity resin compositions can be realized whose biocompatibility, chemical/physical properties, and ratio of critical energy to laser penetration depth can particularly satisfy the requirements of the above-described production method and with which additionally particularly smooth surfaces can be produced for the generated shaped bodies.

Moreover, it was also found that by adding a small amount of an anaerobic inhibitor such as 2,2,6,6-tetramethylpiperidin-1-yloxy (free radical) the laser penetration depth and the critical energy of the resin compositions can be advantageously controlled. In addition to good mechanical properties, excellent biocompatibility, and low water absorption, the shaped bodies obtained by curing possess elongation at break figures greater than or equal to 10% and can be post-treated like for instance tumbled, ground, or enameled. The smooth surface has proved to be advantageous since e.g. during the tumbling process the material removed and thus the tumble times can be reduced. Consequently, process costs are lower with increased shape accuracy and thus fit accuracy for the produced earpiece, for instance.

The subject of the present invention is consequently a low-viscosity, radiation-curable resin composition for use in PNP technology or in the above-described generative production technologies by means of which antimicrobial objects can be produced, containing:

0-75 wt. % of one or a plurality of monomeric/oligomeric urethane(meth)acrylates having a functionality of n<4, viscosity <30 Pa s, and molecular weight <3500;

b) 0-45 wt. % of a monomeric or oligomeric dimethacrylate based on bisphenol A or bisphenol F and or of a monomeric aliphatic or cycloaliphatic di(meth)acrylate having a viscosity <6 Pa s;

c) 0-25 wt. % of an n-fold cross-linking monomeric or oligomeric component, characterized by n is greater than or equal to 3 meth- and/or acrylate function;

d) 0-15 wt. % of one or a plurality of monofunctional (meth)acrylates;

e) 0.01-5 wt. % of one or a combination of antimicrobial additives from the groups of antimicrobially active glass fillers or silver particles;

f) 0.5-6 wt. % of one or a combination of a plurality of photoinitiators whose absorption is in the wavelength range of the laser beam used or of the radiation source;

g) 0-0.5 wt. % of one or a plurality of anaerobic inhibitors;

h) 0-10 wt. % fillers;

i) 0-5 wt. % coloring agents;

j) 0-5 wt. % conventional additives such as UV stabilizers or flow agents, the proportion of components a) through j) together equaling 100 wt. %.

Preferably the inventive mixture contains:

a) 20-75 wt. % of one or a plurality of aliphatic or cycloaliphatic monomeric/oligomeric urethane(meth)acrylates having a functionality n<4, viscosity <15 Pa s and molecular weight <2000;

b) 5-25 wt. % of an n-fold ethoxylated bisphenol-a-dimethacrylate having an ethoxylation degree >10 or of a mixture of n-fold ethoxylated bisphenol-a-dimethacrylates having an ethoxylation degree $\leq 30$;

c) 2.5-10 wt. % of an n-fold cross-linking monomeric or oligomeric component, characterized by n is greater than or equal to 4 meth- and/or acrylate functions having a viscosity $\leq 20$ Pa s;

d) 4-15 wt. % of one or a plurality of monofunctional (meth)acrylates having a viscosity <3 Pa s;

e) 1-4 wt. % of antimicrobially acting glass filler, comprising 45±5 wt. % $SiO_2$, 25±5 wt. % $Na_2O$, 25±5 wt. % CaO, and 5±5 wt. % $P_2O_5$ or a combination of antimicrobial additives from the groups of antimicrobially acting glass fillers or silver nanoparticles;

f) 1-4.5 wt. % of one or a combination of a plurality of photoinitiators whose absorption is in the wavelength range of the laser beam or radiation source used;

g) 0-0.5 wt. % of one or a combination of anaerobic inhibitors, also in conjunction with those aerobic inhibitors known to one skilled in the art of stereolithograpy;

h) 0-10 wt. % fillers;

i) 0-4 wt. % dyes;

j) 0.01-3 wt. % conventional additives such as UV stabilizers or flow agents, the proportion of components a) through j) together equaling 100 wt. %.

More preferably, the inventive mixture contains:

a) 20-75 wt. % of one or a plurality of aliphatic or cycloaliphatic monomeric/oligomeric urethane(meth)acrylates having an acrylate functionality of <4, viscosity <15 Pa s, and molecular weight <2000;

b) 5-25 wt. % of an ethoxylated bisphenol-A-dimethacrylate having an ethoxylation degree >10 or of a mixture of ethoxylated bisphenol-a-dimethacrylates having an ethoxylation degree $\leq 30$, wherein the ethoxylated bisphenol-A-dimethacrylates are selected from the group consisting of bisphenol-A-ethoxylate(2)dimethacrylate, bisphenol-A-ethoxylate(4) dimethacrylate, bisphenol-A-propoxylate(2) dimethacrylate, bisphenol-A-propoxylate(4)dimethacrylate, and mixtures thereof;

c) 2.5-10 wt. % of a cross-linking monomeric or oligomeric component, wherein the component contains 4 methacrylate and/or acrylate functionalities and has a viscosity $\leq 20$ Pa s;

d) 4-15 wt. % of one or a plurality of monofunctional (meth)acrylates with a viscosity <3 Pa·s;

e) 1-2 wt. % of an antimicrobially acting glass filler comprising 45 wt. % $SiO_2$, 25 wt. % $Na_2O$, 25 wt. % CaO, and 5 wt. % $P_2O_5$ based on 100 wt % glass filler;

f) 0.01-1 wt. % of silver particles having a particle diameter <30 nm;

g) 1-4.5 wt. % of one or a plurality of photoinitiators, whose absorption is in the wavelength range of an $ND:YVO_4$ laser beam used or of an actinic radiation source used to promote free radical formation;

h) 0-0.5 wt. % of one or a plurality of anaerobic inhibitors, in conjunction with those aerobic inhibitors acceptable in the art of stereolithograpy;

I) 0-10 wt. % fillers;

j) 0-4 wt. % dyes;

k) 0.01-3 wt. % conventional additives selected from the group consisting of stabilizers and flow agents, the proportion of components a) through j) together equaling 100 wt. %.

The urethane(meth)acrylates with a functionality <4 used in the inventive compositions as component (a) are known to one skilled in the art and can be produced in a known manner in that for instance a hydroxyl-terminated polyurethane is reacted with methacrylic acid to form urethane methacrylate or in that an isocyanate-terminated prepolymer is reacted with hydroxymethacrylates. Such methods are known e.g. from EP 0579503.

Urethane(meth)acrylates can also be obtained commercially and are sold for example by Piccadilly Chemicals under the tradename PC-Cure®, by Sartomer under the tradename CN 1963, by Cognis under the tradename Photomer, by UCB under the tradename Ebecryl, and by Rhan under the tradename Genomer®.

Preferably used for urethane(meth)acrylates are those that are functionalized n<4, possess a viscosity <15 Pa s, have a molecular weight <2000, and have been produced from aliphatic educts. In particular the isomer mixture 7,7,9-(or 7,9,9-)-trimethyl-4,13-dioxo-13,14-dioxa-5,12-diazahexadecane-1,16-diol-dimethacrylate obtained from HEMA and TMDI is used.

Compounds that are suitable for component (b) are for instance dimethacrylates of the (n)-alkoxylated bisphenol A such as bisphenol-A-ethoxylate(2)dimethacrylate, bisphenol-A-ethoxylate(4)dimethacrylate, bisphenol-A-propoxylate(2)dimethacrylate, bisphenol-A-propoxylate(4) dimethacrylate, as well as dimethacrylates of the (n)-alkoxylated bisphenol F such as bisphenol-F-ethoxylate(2) dimethacrylate and bisphenol-F-ethoxylate(4) dimethacrylate, bisphenol-F-propoxylate(2)dimethacrylate, bisphenol-F-propoxylate(4)dimethacrylate, and mixtures thereof. Preferably used are monomeric or oligomeric dimethacrylates based on bisphenol A, in particular bisphenol-A-ethoxylate(10)dimethacrylate and bisphenol-A-ethoxylate(30)dimethacrylate. In addition, compounds that can be used for component (b) are for example: 1,3-butanediol dimethacrylate, 1,6-hexanediol dimethacrylate, 1,3-butylene glycol dimethacrylate, diethylene glycol dimethacrylate, ethylene glycol dimethacrylate, neopentyl dimethacrylate, polyethylene glycol dimethacrylate, triethylene glycol dimethacrylate, and tetraethylene glycol dimethacrylate, and preferably 1,4-butanediol dimethacrylate. Such products can be obtained commercially, for instance from Sartomer Company.

Compounds that can be used for component (c) are for instance di-trimethylolpropane tetra(meth)acrylate, dipentaerythritol-penta(meth)acrylate, n-fold ethoxylated dipentaerythritol-penta(meth)acrylate, pentaerythritol tetra(meth) acrylate. Such products can be obtained commercially, for instance from Sartomer Company.

Compounds that can be used for component (d) are for instance:

2(2-ethoxyethoxy)ethyl(meth)acrylate, phenoxyethyl(meth)acrylate, C12-C18alkyl(meth)acrylates, caprolactone (meth)acrylate, isobornyl (meth)acrylate, isodecyl(meth)acrylate, lauryl(meth)acrylate, polypropylene glycol (methacrylate), tetrahydrofurfuryl (meth)acrylate.

Used for component (e) are antimicrobially active glass fillers in the presence of moisture that comprise 45±5 wt. % $SiO_2$, 25±5 wt. % $Na_2O$, 25±5 wt. % CaO, and 5±5 wt. % $P_2O_5$, having a particle size <100 mm, as are sold for instance by the Schott Company, individually or in combination with Ag nanoparticles as can be obtained commercially from Ciba or AgPure, for example. The modes of action for the bacteriostatic effects of the described additives are manifold (pH control, change in the osmotic pressure on the cell membrane, potassium ion exchange, and irreversible reactions with thio-containing proteins). These are known to one skilled in the art and can be studied in the relevant literature.

Photoinitiators of all types can be used for component (f) that form free radicals with the appropriate irradiation. Known photoinitiators are compounds of benzoins, benzoin ethers such as benzoin, benzoin methyl ether, benzoin ethyl ether, and benzoin isopropyl ether, benzoin phenyl ether, and benzoin acetate, acetophenones such as acetophenone, 2,2-dimethyoxyacetophenone and 1,1-dichloroacetophenone, benzil, benzil ketals such as benzil dimethyl ketal and benzil diethyl ketal, anthraquinones such as 2-methyl anthraquinone, 2-ethyl anthraquinone, 2-tert.-butyl anthraquinone, 1-chloroanthraquinone, and 2-amylanthraquinone, triphenylphosphine, benzoylphosphine oxides such as for instance 2,4,6-trimethylbenzoyldiphenylphosphine oxide (Luzirin TPO) and bis(2,4,6-trimethylbenzoylphenyl)-phosphine oxide, benzophenones such as benzophenone and 4,4'-bis-(N,N'-dimethylamino)-benzophenone, thioxanthones and xanthones, acridin derivatives, phenazine derivatives, quinoxaline derivatives, or 1-phenyl-1,2-propandion-2-O-benzoyloxime, 1-aminophenyl ketones or 1-hydroxyphenyl ketones such as 1-hydroxycyclohexyl phenyl ketone, phenyl-(1-hydroxyisopropyl)-ketone, and 4-isopropylphenyl-(1-hydroxyisopropyl)-ketone.

Particularly preferred compounds that are used in combination with an $ND:YVO_4$ solid-state laser are bis(2,4,6-trimethylbenzoyl)-phenylphosphine oxide, 2,4,6-trimethylbenzoyldiphenylphosphine oxide, 2-hydroxy-2-methylpropiophenone, hydroxycyclohexyl phenyl ketone, and mixtures of these photoinitiators.

The 2,2,6,6-tetramethylpiperidin-1-yloxy (free radical), phenothiazine (PTZ), 2,2-diphenyl-1-picrylhydrazyl radical (DPPH), or a combination of these inhibitors can be added to the inventive mixtures (g) for adjusting the laser penetration depth and the critical energy.

The fillers and additives known to one skilled in the art, for instance flow-control agents, UV stabilizers, wetting agents, fillers, dyes, and pigments, can be added to the inventive mixtures, where required. In the context of the invention, anthraquinone dyes as are sold e.g. by Bayer under the Macrolex® name are particularly suitable dyes.

The compositions for inventive, translucent resin mixtures can be taken from examples 1-6, in variants with and without added microbial glass fillers, as they could be used e.g. for producing otoplastics.

EXAMPLE 1

A Colorless, Translucent Stereolithography Resin Having Antimicrobial Properties 65.6 wt. % 7,7,9-(or 7,9,9-)trimethyl-4,13-dioxo-3,14-dioxa-5,12-diazahexadecane-1,16-diol-dimethacrylate
14.672 wt. % bisphenol-A-ethoxylate(30)dimethacrylate
4.8 wt. % dipentaerythritol-penta(meth)acrylate
4.6 wt. % 1,6-hexanediol dimethacrylate
4.6 wt. % lauryl methacrylate methacrylate
3 wt. % 1-hydroxycyclohexyl phenyl ketone
1.5 wt. % glass filler, comprising 45±5 wt. % $SiO_2$, 25±5 wt. % $Na_2O$, 25±5 wt. % CaO, and 5±5 wt. % $P_2O_5$
1 wt. % 2-hydroxy-2-methyl-1-phenylpropanone
0.2 wt. % 2,4,6-trimethylbenzoyldiphenylphosphine oxide
0.025 wt. % UV stabilizer
0.003 wt. % 2,2,6,6-tetramethylpiperidin-1-yloxy (free radical)

EXAMPLE 2

A Colorless, Translucent Stereolithography Resin with no Antimicrobial Additives 66.62 wt. % 7,7,9-(or 7,9,9-)trimethyl-4,13-dioxo-3,14-dioxa-5,12-diazahexadecane-1,16-diol-dimethacrylate
14.92 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
3 wt. % 1-hydroxycyclohexyl phenyl ketone
1 wt. % 2-hydroxy-2-methyl-1-phenylpropanone
0.2 wt. % 2,4,6-trimethylbenzoyldiphenylphosphine oxide
0.025 wt. % UV stabilizer
0.003 wt. % 2,2,6,6-tetramethylpiperidin-1-yloxy (free radical)

EXAMPLE 3

A Red, Translucent Stereolithography Resin Having Antimicrobial Properties 67.65 wt. % 7,7,9-(or 7,9,9-)trimethyl-4,13-dioxo-3,14-dioxa-5,12-diazahexadecane-1,16-diol-dimethacrylate
15 wt. % bisphenol-A-ethoxylate(30)dimethacrylate
4.9 wt. % dipentaerythritol-penta(meth)acrylate
4.7 wt. % 1,6-hexanediol dimethacrylate
4.7 wt. % lauryl methacrylate
1.5 wt. % 2,4,6-trimethylbenzoyldiphenylphosphine oxide
1.5 wt. % glass filler, comprising 45±5 wt. % $SiO_2$, 25±5 wt. % $Na_2O$, 25±5 wt. % CaO, and 5±5 wt. % $P_2O_5$
0.025 wt. % UV stabilizer
0.012 wt. % azo dye red H
0.003 wt. % 2,2,6,6-tetramethylpiperidin-1-yloxy (free radical)

EXAMPLE 4

A Red, Translucent Stereolithography Resin with no Antimicrobial Additives 69.15 wt. % 7,7,9-(or 7,9,9-)trimethyl-4,13-dioxo-3,14-dioxa-5,12-diazahexadecane-1,16-diol-dimethacrylate 15 wt. % bisphenol-A-ethoxylate(30)dimethacrylate
4.9 wt. % dipentaerythritol-penta(meth)acrylate
4.7 wt. % 1,6-hexanediol dimethacrylate
4.7 wt. % lauryl methacrylate
1.5 wt. % 2,4,6-trimethylbenzoyldiphenylphosphine oxide
0.025 wt. % UV stabilizer
0.012 wt. % azo dye red H
0.003 wt. % 2,2,6,6-tetramethylpiperidin-1-yloxy (free radical)

EXAMPLE 5

A Blue, Translucent Stereolithography Resin Having Antimicrobial Properties 67.65 wt. % 7,7,9-(or 7,9,9-)trimethyl-4,13-dioxo-3,14-dioxa-5,12-diazahexadecane-1,16-diol-dimethacrylate
15 wt. % bisphenol-A-ethoxylate(30)dimethacrylate
4.9 wt. % dipentaerythritol-penta(meth)acrylate
4.7 wt. % 1,6-hexanediol dimethacrylate 4.7 wt. % lauryl methacrylate
1.5 wt. % 2,4,6-trimethylbenzoyldiphenylphosphine oxide
1.5 wt. % glass filler, comprising 45±5 wt. % $SiO_2$, 25±5 wt. % $Na_2O$, 25±5 wt. % CaO, and 5±5 wt. % $P_2O_5$
0.025 wt. % UV stabilizer
0.03 wt. % anthraquinone dye preparation (incl. C.I. Solvent Blue 97)
0.003 wt. % 2,2,6,6-tetramethylpiperidin-1-yloxy (free radical)

EXAMPLE 6

A Blue, Translucent Stereolithography Resin with no Microbial Additives 68.55 wt. % 7,7,9-(or 7,9,9-)trimethyl-4,13-dioxo-3,14-dioxa-5,12-diazahexadecane-1,16-diol-dimethacrylate
15.3 wt. % bisphenol-A-ethoxylate(30)dimethacrylate
5 wt. % dipentaerythritol-penta(meth)acrylate
4.8 wt. % 1,6-hexanediol dimethacrylate 4.8 wt. % lauryl methacrylate
1.5 wt. % 2,4,6-trimethylbenzoyldiphenylphosphine oxide
0.025 wt. % UV stabilizer
0.03 wt. % anthraquinone dye preparation (incl. C.I. Solvent Blue 97)
0.003 wt. % 2,2,6,6-tetramethylpiperidin-1-yloxy (free radical)

The chemico-physical data for the sample compositions are reproduced in Table 1.

TABLE 1

Parameters of stereolithography compositions from Example 1 through Example 6

| Property | Ex. 1 | Ex. 2 | Ex. 3 | Ex. 4 | Ex. 5 | Ex. 6 |
|---|---|---|---|---|---|---|
| Viscosity at 23° C., mPa s | 1000 | 1060 | 1240 | 1120 | 1180 | 1070 |
| E-module of cured shaped body, N $mm^{-2}$ | 1739 | 1739 | 2002 | 1963 | 2033 | 1978 |
| Flexural strength of cured shaped body, N $mm^2$ | 97 | 98 | 112 | 110 | 112 | 113 |
| Elongation at break of cured shaped body, % | 11 | 11 | 11 | 11 | 10 | 10 |
| Ec, mJ $cm^{-2}$ | 21 | 20.9 | 14.5 | 14 | 14.4 | 14.4 |
| Dp, mils | 6.6 | 5.4 | 6.3 | 5.1 | 5.7 | 5.6 |

The parameters of the above resins that are relevant for stereolithography are listed in Table 1. All of the viscosity measurements were performed at 23° C. with a CVO 120-rheometer from Bohlin Instruments. The flexural strength, E-module, and elongation determinations were made using EN ISO 178 (1996) with a Zwick 1-Testmaschine from Zwick. The means from 10 windowpane specimens were used to determine the Ec and Dp by means of the above windowpane method. The specimens were produced with a Viper $si^2$ SLA system (3D Systems), fitted with an $Nd:YVO_4$ solid-state laser. The green compacts were cured with the Sonolux PR stroboscope light unit from Innovation Meditech, 2×4800 flashes.

It can be seen from Table 1 that the addition of the antimicrobially acting glass filler, within measurement accuracies, attains results comparable to the systems with no glass filler. In a direct comparison to the unfilled system, however, shaped bodies are obtained with the filled systems that have substantially more homogeneous surfaces. Furthermore, the addition of glass filler results in a slight increase in the laser penetration depth. This effect can be used in terms of higher stratum thickness and thus shorter construction times. Moreover, it can be seen from Table 1 that resin compositions are obtained, in particular by the addition of the antimicrobially acting filler, that are superior to the prior art (see Table 2) in the entirety of their mechanical values.

TABLE 2

Mechanical values of commercially available products for producing earpieces

| Material | E-module, N $mm^{-2}$ | Flexural strength, N $mm^{-2}$ | Elongation at break % |
|---|---|---|---|
| Fotoplast S/IO Blue, transparent, Lot. 201504 | 1513 | 81 | 10 |
| Fotoplast S/IO Red, transparent Lot. 301531 | 1527 | 84 | 13 |
| Fotoplast S/IO Colorless Transparent, Lot. 203523 | 1602 | 88 | 11 |
| Fotoplast S/IO Yellowish, Lot. 301515 | 1586 | 80 | 13 |

In addition to translucent stereolithography resin compositions, opaque compositions are also frequently used e.g. for constructing hearing aid shells.

EXAMPLE 7

A Beige, Opaque Stereolithography Resin with Antimicrobial Glass Fillers 66.84 wt. % 7,7,9-(or 7,9,9-)trimethyl-4,13-dioxo-3,14-dioxa-5,12-diazahexadecane-1,16-diol-dimethacrylate 14.92 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
2.0 wt. % glass filler, comprising 45±5 wt. % $SiO_2$, 25±5 wt. % $Na_2O$, 25±5 wt. % CaO, and 5±5 wt. % $P_2O_5$
1.5 wt. % phenyl bis(2,4,6-trimethylbenzoyl)-phosphine oxide
0.025 wt. % UV stabilizer
0.5 wt. % iron oxide pigments
0.003 wt. % 2,2,6,6-tetramethylpiperidin-1-yloxy (free radical)

EXAMPLE 8

A Beige, Opaque Stereolithography Resin without Antimicrobial Glass Fillers 66.84 wt. % 7,7,9-(or 7,9,9-)trimethyl-4,13-dioxo-3,14-dioxa-5,12-diazahexadecane-1,16-diol-dimethacrylate
14.92 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
1.5 wt. % phenyl bis(2,4,6-trimethylbenzoyl)-phosphine oxide
0.025 wt. % UV stabilizer 0.5 wt. % iron oxide pigments
0.003 wt. % 2,2,6,6-tetramethylpiperidin-1-yloxy (free radical)

In opaque compositions, preferably silver particles can be added in a concentration range from 0.1 to 1 wt. % as an antimicrobially acting addition.

EXAMPLE 9

A Beige, Opaque Stereolithography Resin with Antimicrobially Acting Silver Particles 68.74 wt. % 7,7,9-(or 7,9,9-)trimethyl-4,13-dioxo-3,14-dioxa-5,12-diazahexadecane-1,16-diol-dimethacrylate
14.92 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
1.5 wt. % phenyl bis (2,4,6-trimethylbenzoyl)-phosphine oxide
0.025 wt. % UV stabilizer
0.5 wt. % iron oxide pigments 0.1 wt. % nano-silver (particle size <30 nm)
0.003 wt. % 2,2,6,6-tetramethylpiperidin-1-yloxy (free radical)

EXAMPLE 10

A Beige, Opaque Stereolithography Resin with Antimicrobially-Acting Silver Particles 68.54 wt. % 7,7,9-(or 7,9,9-)trimethyl-4,13-dioxo-3,14-dioxa-5,12-diazahexadecane-1,16-diol-dimethacrylate
14.92 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
1.5 wt. % phenyl bis(2,4,6-trimethylbenzoyl)-phosphine oxide
0.025 wt. % UV stabilizer
0.5 wt. % iron oxide pigments
0.3 wt. % nano-silver (particle size <30 nm)
0.003 wt. % 2,2,6,6-tetramethylpiperidin-1-yloxy (free radical)

EXAMPLE 11

A Beige, Opaque Stereolithography Resin with Antimicrobially Acting Silver Particles 67.84 wt. % 7,7,9-(or 7,9,9-)trimethyl-4,13-dioxo-3,14-dioxa-5,12-diazahexadecane-1,16-diol-dimethacrylate
14.92 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
1.5 wt. % phenyl bis(2,4,6-trimethylbenzoyl)-phosphine oxide
0.025 wt. % UV stabilizer
0.5 wt. % iron oxide pigments
1 wt. % nano-silver (particle size <30 nm)
0.003 wt. % 2,2,6,6-tetramethylpiperidin-1-yloxy (free radical)

TABLE 3

Parameters of beige opaque stereolithography compositions from Example 7 through Example 11

| Property | Ex. 7 | Ex. 8 | Ex. 9 | Ex. 10 | Ex. 11 |
| --- | --- | --- | --- | --- | --- |
| Viscosity at 23° C., mPa s | 1270 | 1320 | 1200 | 1220 | 1220 |
| E-module of cured shaped body, N $mm^{-2}$ | 1978 | 1998 | 1932 | 1857 | 1852 |
| Flexural strength of cured shaped body, N $mm^2$ | 113 | 99 | 103 | 106 | 103 |
| Elongation at break of cured shaped body, % | 13 | 7 | 10 | 11 | 10 |
| Ec, mJ $cm^{-2}$ | 9.4 | 15.9 | 13 | 11 | 11.7 |
| Dp, mils | 3.8 | 2.0 | 3.2 | 2.9 | 2.6 |

It can be seen from the data entered in Table 3 that Examples 7-11 also lead to stereolithography resins that can be advantageously used for producing hearing aid shells. Moreover, it was found that the elongation at break figures for the above resin mixtures increase by 3% when the specimens are produced by means of the stereolithography process. In one particular embodiment, the resin mixtures contain silver particles in addition to an antimicrobially acting glass filler (Examples 12-14).

EXAMPLE 12

A Beige, Opaque Stereolithography Resin with Antimicrobially Acting Silver Particles and Glass Fillers 67.74 wt. % 7,7,9-(or 7,9,9-)trimethyl-4,13-dioxo-3,14-dioxa-5,12-diazahexadecane-1,16-diol-dimethacrylate
14.42 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
1.5 wt. % phenyl bis(2,4,6-trimethylbenzoyl)-phosphine oxide
1.5 wt. % glass filler, comprising 45±5 wt. % $SiO_2$, 25±5 wt. % $Na_2O$, 25±5 wt. % CaO, and 5±5 wt. % $P_2O_5$
0.025 wt. % UV stabilizer 0.5 wt. % iron oxide pigments
0.1 wt. % nano-silver (particle size <30 nm)
0.003 wt. % 2,2,6,6-tetramethylpiperidin-1-yloxy (free radical)

EXAMPLE 13

A Beige, Opaque Stereolithography Resin with Antimicrobially Acting Silver Particles and Glass Fillers 67.54 wt. % 7,7,9-(or 7,9,9-)trimethyl-4,13-dioxo-3,14-dioxa-5,12-diazahexadecane-1,16-diol-dimethacrylate
14.42 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
1.5 wt. % phenyl bis(2,4,6-trimethylbenzoyl)-phosphine oxide
1.5 wt. % glass filler, comprising 45±5 wt. % $SiO_2$, 25±5 wt. % $Na_2O$, 25±5 wt. % CaO, and 5±5 wt. % $P_2O_5$
0.025 wt. % UV stabilizer
0.5 wt. % iron oxide pigments
0.3 wt. % nano-silver (particle size <30 nm)
0.003 wt. % 2,2,6,6-tetramethylpiperidin-1-yloxy (free radical)

EXAMPLE 14

A Beige, Opaque Stereolithography Resin with Antimicrobially Acting Silver Particles and Glass Filler 66.84 wt. % 7,7,9-(or 7,9,9-)trimethyl-4,13-dioxo-3,14-dioxa-5,12-diazahexadecane-1,16-diol-dimethacrylate
14.42 wt. % bisphenol-A-ethoxylate(30)dimethacrylate
4.88 wt. % dipentaerythritol-penta(meth)acrylate
4.68 wt. % 1,6-hexanediol dimethacrylate
4.68 wt. % lauryl methacrylate
1.5 wt. % phenyl bis(2,4,6-trimethylbenzoyl)-phosphine oxide
1.5 wt. % glass filler, comprising 45±5 wt. % $SiO_2$, 25±5 wt. % $Na_2O$, 25±5 wt. % CaO, and 5±5 wt. % $P_2O_5$
0.025 wt. % UV stabilizer
0.5 wt. % iron oxide pigments
1 wt. % nano-silver (particle size <30 nm)
0.003 wt. % 2,2,6,6-tetramethylpiperidin-1-yloxy (free radical)

The chemico-physical data for the sample compositions are reproduced in Table 4.

Tab. 4: Parameters of beige opaque stereolithography resin compositions from Example 12 through Example 14, which contain both silver particles and glass fillers with antimicrobial action:

TABLE 4

Parameters of beige opaque stereolithography resin compositions from Example 12 through Example 14, which contain both silver particles and glass fillers with antimicrobial action:

| Property | Ex. 12 | Ex. 13 | Ex. 14 |
|---|---|---|---|
| Viscosity at 23° C., mPa s | 1470 | 1350 | 1370 |
| E-module of cured shaped body, N $mm^{-2}$ | 1956 | 1897 | 1854 |
| Flexural strength of cured shaped body, N $mm^2$ | 105 | 100 | 96 |
| Elongation at break of cured shaped body, % | 10 | 9 | 9 |
| Ec, mJ $cm^{-2}$ | 9.2 | 10.3 | 9.8 |
| Dp, mils | 3.1 | 2.9 | 2.6 |

It can clearly be seen from the data entered in Table 4 that Examples 12-14 also lead to stereolithography resins that can be advantageously used for producing hearing aid shells. Moreover, it was found that the elongation at break figures for the above resin mixtures increase by 3% when the specimens are produced by means of the stereolithography process. Thus low-viscosity resin mixtures are provided by means of which earpieces can be produced that are characterized in all of their mechanical properties by high values and that simultaneously have a surface that is largely smoother than the prior art and that has antimicrobial action. Consequently the earpieces do not have to be protected by complex enameling processes prior to colonization with biofilms.

The invention claimed is:

1. A biocompatible, low-viscosity, radiation-curable composition, for producing antimicrobial medical products, in particular earpieces, by means of positive-negative-positive production methods or stereolithography, containing:
   a) 20-75 wt. % of one or a plurality of monomeric/oligomeric urethane(meth)acrylates having an acrylate functionality of <4, viscosity <30 Pa s, and molecular weight <3500;
   b) 5-45 weight % of a monomeric or oligomeric dimethacrylate of bisphenol A or bisphenol F and or of a monomeric aliphatic or cycloaliphatic di(meth)acrylate having a viscosity <6 Pa s;
   c) 2.5-25 weight % of a cross-linking monomeric or oligomeric component, wherein the component contains 4 methacrylate and/or acrylate functionalities;
   d) 0-15 wt. % of one or a plurality of monofunctional (meth)acrylates;
   e) 0.01-5 wt. % of one or a combination of antimicrobial additives selected from the group consisting of antimicrobially active glass fillers and silver particles;
   f) 0.5-6 wt. % of one or a plurality of photoinitiators whose absorption is in the wavelength range of an $ND:YVO_4$ laser beam used or of an actinic radiation source used to promote free radical formation;
   g) 0-0.5 wt. % of one or a plurality of anaerobic inhibitors;
   h) 0-10 wt. % fillers;
   I) 0-5 wt. % coloring agents; and
   j) 0-5 wt. % conventional additives selected from the group consisting of ultraviolet stabilizers and flow agents, the proportion of components a) through j) together equaling 100 wt. %.

2. The composition in accordance with claim 1, containing
   a) 20-75 wt. % of one or a plurality of aliphatic or cycloaliphatic monomeric/oligomeric urethane(meth) acrylates having an acrylate functionality <4, viscosity <15 Pa s and molecular weight <2000;

b) 5-25 wt. % of ethoxylated bisphenol-A-dimethacrylate having an ethoxylation degree >10 or of a mixture of ethoxylated bisphenol-A-dimethacrylates having an ethoxylation degree ≦30, wherein the ethoxylated bisphenol-A-dimethacrylates are selected from the group consisting of bisphenol-A-ethoxylate(2)dimethacrylate, bisphenol-A-ethoxylate(4)dimethacrylate, bisphenol-A-propoxylate(2)dimethacrylate, bisphenol-A-propoxylate(4)dimethacrylate, and mixtures thereof;

c) 2.5-10 wt. % of a cross-linking monomeric or oligomeric component, wherein the component contains 4 methacrylate and/or acrylate functionalities and has a viscosity ≦20 Pa s;

d) 4-15 wt. % of one or a plurality of monofunctional (meth)acrylates having a viscosity <3 Pa·s;

e) 1-4 wt. % of antimicrobially acting glass filler, comprising 45±5 wt. % $SiO_2$, 25±5 wt. % $Na_2O$, 25±5 wt. % CaO, and 5±5 wt. % $P_2O_5$ based on 100 wt. % glass filler or a combination of antimicrobial additives selected from the group consisting of antimicrobially acting glass fillers and silver nanoparticles;

f) 1-4.5 wt. % of one or a plurality of photoinitiators whose absorption is in the wavelength range of an ND:YVO$_4$ laser beam or an actinic radiation source used to promote free radical formation;

g) 0-0.5 wt. % of one or a plurality of anaerobic inhibitors, in conjunction with those aerobic inhibitors acceptable in the art of stereolithograpy;

h) 0-10 wt. % fillers;

I) 0-4wt. % dyes;

j) 0.01-3 wt. % conventional additives selected from the group consisting of stabilizers and flow agents, the proportion of components a) through j) together equaling 100 wt. %.

3. The composition in accordance with claim 1, containing a) 20-75 wt. % of one or a plurality of aliphatic or cycloaliphatic monomeric/oligomeric urethane(meth)acrylates having an acrylate functionality of <4, viscosity <15 Pa s, and molecular weight <2000;

b) 5-25 wt. % of an ethoxylated bisphenol-A-dimethacrylate having an ethoxylation degree >10 or of a mixture of ethoxylated bisphenol-a-dimethacrylates having an ethoxylation degree ≦30, wherein the ethoxylated bisphenol-A-dimethacrylates are selected from the group consisting of bisphenol-A-ethoxylate(2)dimethacrylate, bisphenol-A-ethoxylate(4)dimethacrylate, bisphenol-A-propoxylate(2)dimethacrylate, bisphenol-A-propoxylate(4)dimethacrylate, and mixtures thereof;

c) 2.5-10 wt. % of a cross-linking monomeric or oligomeric component, wherein the component contains 4 methacrylate and/or acrylate functionalities and has a viscosity ≦20 Pa s;

d) 4-15 wt. % of one or a plurality of monofunctional (meth)acrylates with a viscosity <3 Pa·s;

e) 1-2 wt. % of an antimicrobially acting glass filler comprising 45 wt. % $SiO_2$, 25 wt. % $Na_2O$, 25 wt. % CaO, and 5 wt. % $P_2O_5$ based on 100 wt % glass filler;

f) 0.01-1 wt. % of silver particles having a particle diameter <30 nm;

g) 1-4.5 wt. % of one or a plurality of photoinitiators, whose absorption is in the wavelength range of an ND:YVO$_4$ laser beam used or of an actinic radiation source used to promote free radical formation;

h) 0-0.5 wt. % of one or a plurality of anaerobic inhibitors, in conjunction with those aerobic inhibitors acceptable in the art of stereolithography;

I) 0-10 wt. % fillers;

j) 0-4 wt. % dyes;

k) 0.1-3 wt. % conventional additives selected from the group consisting of stabilizers and flow agents, the proportion of components a) through j) together equaling 100 wt. %.

* * * * *